United States Patent
Brac De La Perriere et al.

(10) Patent No.: US 11,369,560 B2
(45) Date of Patent: *Jun. 28, 2022

(54) COSMETIC PROCESS FOR TREATING KERATIN FIBRES, COMPRISING THE APPLICATION OF A BASE COMPOSITION AND A COMPOSITION COMPRISING A CATIONIC SURFACTANT

(71) Applicant: L'OREAL, Paris (FR)

(72) Inventors: Anne-Sophie Brac De La Perriere, Saint Ouen (FR); Sandrine Maggio, Saint Ouen (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/497,577

(22) PCT Filed: Mar. 30, 2018

(86) PCT No.: PCT/EP2018/058304
§ 371 (c)(1),
(2) Date: Sep. 25, 2019

(87) PCT Pub. No.: WO2018/178341
PCT Pub. Date: Oct. 4, 2018

(65) Prior Publication Data
US 2020/0022902 A1    Jan. 23, 2020

(30) Foreign Application Priority Data

Mar. 31, 2017   (FR) ..................................... 1752806

(51) Int. Cl.
*A61K 8/41* (2006.01)
*A61K 8/49* (2006.01)
*A61K 8/894* (2006.01)
*A61Q 5/12* (2006.01)

(52) U.S. Cl.
CPC .............. *A61K 8/894* (2013.01); *A61K 8/416* (2013.01); *A61K 8/4946* (2013.01); *A61Q 5/12* (2013.01)

(58) Field of Classification Search
CPC .............. A61K 2800/882; A61K 8/894; A61K 8/4946; A61K 8/416; A61Q 5/12
See application file for complete search history.

(56) References Cited

U.S. PATENT DOCUMENTS

| | | | |
|---|---|---|---|
| 5,972,322 A | 10/1999 | Rath et al. | |
| 6,039,933 A | * 3/2000 | Samain | A61K 8/8147 424/47 |
| 6,117,436 A | * 9/2000 | Flemming | A61K 8/342 424/400 |
| 6,399,050 B1 | * 6/2002 | Pasquet | A61K 8/891 424/70.12 |
| 6,589,538 B1 | * 7/2003 | Lemann | A61K 8/585 424/401 |
| 2007/0166258 A1 | * 7/2007 | Pratley | A61Q 5/06 424/70.7 |

FOREIGN PATENT DOCUMENTS

| | | | |
|---|---|---|---|
| GB | 2 155 788 A | 10/1985 | |
| WO | WO 00/07550 A1 | 2/2000 | |
| WO | WO2009158443 | * 12/2009 | |
| WO | WO 2015/024078 A1 | 2/2015 | |

OTHER PUBLICATIONS

Lem et al; titel: Selecting the perfect silicone for your formulation, Personal care; published Jul. 2014) (Year: 2014).*
Ferdinand Gonzaga et al, title: Morphology-Controlled Synthesis of Poly(oxyethylene)silicone or Alkylsilicone Surfactants with Explicit, Atomically Defined, Branched, Hydrophobic Tails; First published: Dec. 27, 2011. (Year: 2011).*
Mintel, "Conditional for Dry Hair", Database accession No. 10137738, XP002772318.
Mintel, "Repairist Hair Repair Kit", Database accession No. 516283, XP002772319.

* cited by examiner

*Primary Examiner* — Alma Pipic
(74) *Attorney, Agent, or Firm* — Polsinelli PC

(57) ABSTRACT

The present invention relates to a cosmetic process for treating keratin fibres, preferably human keratin fibres such as the hair, in particular for conditioning keratin fibres, using a combination of at least two different compositions, the first composition comprising one or more oxyalkylenated and preferably oxyethylenated silicones and one or more first cationic surfactants, and less than 10% by weight of water relative to the total weight of the composition, and the second composition comprising water and one or more second cationic surfactants. The invention also relates to a kit comprising the two compositions. Finally, the invention relates to a ready-to-use cosmetic composition for treating keratin fibres.

14 Claims, No Drawings

COSMETIC PROCESS FOR TREATING KERATIN FIBRES, COMPRISING THE APPLICATION OF A BASE COMPOSITION AND A COMPOSITION COMPRISING A CATIONIC SURFACTANT

CROSS REFERENCE TO RELATED APPLICATIONS

This application is a National Phase filing under 35 U.S.C. § 371 of PCT/EP2018/058304 filed on Mar. 30, 2018; which application in turn claims priority to Application No. 1752806 filed in France on Mar. 31, 2017. The entire contents of each application are hereby incorporated by reference.

The present invention relates to a cosmetic process for treating keratin fibres, preferably human keratin fibres such as the hair, in particular for conditioning keratin fibres, using a combination of at least two different compositions.

The invention also relates to a kit comprising the two compositions.

Finally, the invention relates to a ready-to-use cosmetic composition for treating keratin fibres.

Hair is generally damaged and embrittled by the action of external atmospheric agents such as light and bad weather, and by mechanical or chemical treatments, such as brushing, combing, dyeing, bleaching, permanent-waving and/or relaxing.

Thus, to overcome these drawbacks, it is now common practice to resort to haircare involving the use of care compositions for conditioning the hair after these treatments so as in particular to give it sheen, softness, suppleness, lightness, a natural feel and also disentangling properties.

These haircare compositions may be, for example, conditioning shampoos or compositions to be applied before or after washing with shampoo, and may be in the form of gels, hair lotions or creams of varying thickness.

Consumers are increasingly in search of personalized treatments prepared just at the time of application in order to specifically reply to their needs, especially when they go to a hairstyling professional. Thus, the use of different compositions, one serving as common base for all consumers, and the other comprising the ingredients intended to give targeted conditioning performance qualities, may be advantageous.

The desired conditioning performance qualities, which may be more or less pronounced from one consumer to another, are especially an improved surface state, ease of disentangling, a smooth feel, coating, improved hair strength and sheen.

It is also appealing to the consumer to assist in the formation of a mixture of textures of cream or care mask type from compositions of entirely different appearance, for example fluid liquid compositions, and to do so by simple mixing using a spatula.

Mixing at the time of use may also make it possible to use in combination ingredients that would be incompatible together in a standard composition.

Thus, the object of the invention is to propose modulable care compositions prepared just before application to the hair, using at least one base composition that is common to all the uses and another composition chosen from a panel as a function of the specific needs of the consumer's hair.

One subject of the invention is thus a cosmetic process for treating keratin fibres, preferably human keratin fibres such as the hair, comprising:

(i) a step of mixing at least:
 a first composition comprising one or more oxyalkylenated, preferably oxyethylenated, silicones, one or more first cationic surfactants, and less than 10% by weight of water relative to the total weight of the composition, and
 a second composition comprising water and one or more second cationic surfactants, so as to obtain a final cosmetic composition, and then
(ii) a step of applying the final cosmetic composition to the keratin fibres.

Thus, the process according to the invention gives treated hair cosmetic qualities, especially an improved surface state, ease of disentangling, a smooth feel, coating, improved hair strength and sheen.

Furthermore, the preparation of the final cosmetic composition in the process according to the invention is easy, by simple mixing of at least two different compositions.

Furthermore, the final composition rinses out easily and quickly.

Another subject of the present invention is a kit comprising at least two compartments:
 a first compartment comprising a first composition as defined above,
 a second compartment comprising a second composition as defined above.

Finally, a subject of the present invention relates to a cosmetic composition for the cosmetic treatment of keratin fibres, comprising:
 i) one or more non-amino oxyalkylenated and preferably non-amino oxyethylenated silicones,
 ii) one or more first cationic surfactants,
 iii) one or more second cationic surfactants different from the cationic surfactants (ii),
 iv) water.

This cosmetic composition advantageously corresponds to the final cosmetic composition obtained on conclusion of the mixing step of the process according to the invention.

The final composition is generally in cream form, has a pleasant texture and is easy to apply and to spread onto keratin fibres.

Other subjects, characteristics, aspects and advantages of the invention will emerge even more clearly on reading the description and the examples that follow.

In the text hereinbelow, and unless otherwise indicated, the limits of a range of values are included within that range, especially in the expressions "between" and "ranging from . . . to . . . ".

Moreover, the expressions "at least one" and "at least" used in the present description are equivalent to the expressions "one or more" and "greater than or equal to", respectively.

According to the present patent application, the term "keratin fibres" mainly denotes human keratin fibres and in particular the hair.

As explained previously, the process according to the invention comprises a step of mixing at least:
 a first composition comprising one or more oxyalkylenated silicones, one or more first cationic surfactants, and less than 10% by weight of water relative to the total weight of the composition, and
 a second composition comprising water and one or more polyols, so as to obtain a final cosmetic composition.

Preferably, the first composition is anhydrous.

For the purposes of the present invention, the term "anhydrous composition" means that this composition comprises less than 10% by weight of water, and preferably less than 9% by weight of water, relative to the total weight of the composition.

Preferably, the oxyalkylenated silicone(s) of the first composition are oxyethylenated.

Advantageously, the oxyalkylenated silicone(s) of the first composition are chosen from non-amino oxyalkylenated silicones, better still from non-amino oxyethylenated silicones.

For the purposes of the present invention, the term "non-amino silicones" means that these silicones do not comprise an amine function in their structure, whether in the form of a primary, secondary or tertiary amine or in the form of a quaternary ammonium group.

According to the invention, the term "oxyalkylenated silicone" denotes any silicone comprising at least one oxyalkylene group of the type $(-C_xH_{2x}O)_a$ in which x may range from 2 to 6 and a is greater than or equal to 1, preferably greater than or equal to 2.

In accordance with the invention, the oxyalkylenated silicones are preferably chosen from the compounds of general formulae (I), (II), (III) and (IV) below:

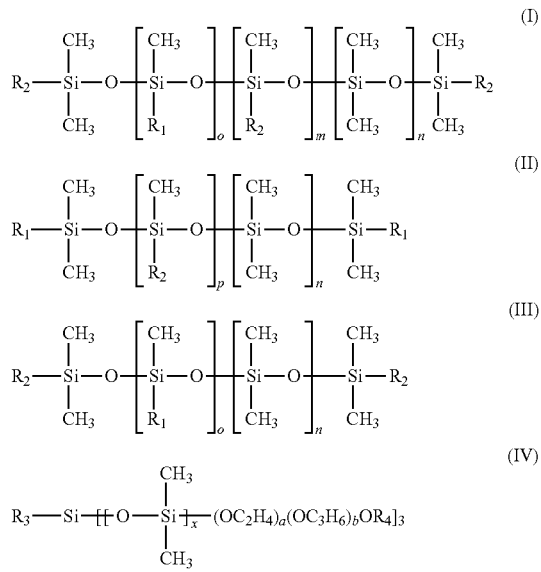

in which formulae (I), (II), (III) and (IV):

$R_1$, which may be identical or different, represents a linear or branched $C_1$-$C_{30}$ alkyl or phenyl radical, $R_2$, which may be identical or different, represents a radical $-C_GH_{2c}-O-(C_2H_4O)_a(C_3H_6O)_b-R_5$ or a radical $-C_cH_{2c}-O-(C_4H_8O)_a-R_5$, $R_3$ and $R_4$, which may be identical or different, denote a linear or branched $C_1$ to $C_{12}$ alkyl radical and preferably a methyl radical, $R_5$, which may be identical or different, is chosen from a hydrogen atom, a linear or branched alkyl radical of 1 to 12 carbon atoms, a linear or branched alkoxy radical of 1 to 6 carbon atoms, a linear or branched acyl radical of 2 to 30 carbon atoms, a radical from among hydroxyl, $-SO_3M$, $C_1$-$C_6$ aminoalkoxy optionally substituted on the amine, $C_2$-$C_6$ aminoacyl optionally substituted on the amine, $-NHCH_2CH_2COOM$, $-N(CH_2CH_2COOM)_2$, aminoalkyl optionally substituted on the amine and on the alkyl chain, $C_2$-$C_{30}$ carboxyacyl, a group optionally substituted with one or two substituted aminoalkyl radicals, $-CO(CH_2)_d COOM$, $-COCHR_7(CH_2)_d COOM$, $-NHCO(CH_2)_d OH$, $-NH_3Y$, a phosphate group, M, which may be identical or different, denotes a hydrogen atom, Na, K, Li, $NH_4$ or an organic amine, $R_7$ denotes a hydrogen atom or a radical $-SO_3M$, d ranges from 1 to 10, m ranges from 0 to 20, n ranges from 0 to 500, o ranges from 0 to 20, p ranges from 1 to 50, a ranges from 0 to 50, b ranges from 0 to 50, a+b is greater than or equal to 2, c ranges from 0 to 4, x ranges from 1 to 100, Y represents a monovalent mineral or organic anion such as halide (chloride or bromide), sulfate or carboxylate (acetate, lactate or citrate), with the proviso that when the silicone is of formula (II) with $R_5$ denoting hydrogen, then n is greater than 12.

Such silicones are sold, for example, by the company Goldschmidt under the trade names Abil WE 09, Abil EM 90, Abil B8852, Abil B8851, Abil B8843 and Abil B8842, by the company Dow Corning under the names Fluid DC 190, DC 3225 C, Q2-5220, Q25354 and Q2-5200, by the company Rhône-Poulenc under the names Silbione Oil 70646 and Rhodorsil Oil 10634, by the company General Electric under the names SF1066 and SF1188, by the company SWS Silicones under the name Silicone Copolymer F 754, by the company Amerchol under the name Silsoft Beauty Aid SL, by the company Shin-Etsu under the name KF 351, by the company Wacker under the name Belsil DMC 6038, by the company Siltech under the names Silwax WD-C, Silwax WD-B, Silwax WD-IS, Silwax WSL, Silwax DCA 100 and Siltech Amine 65, by the company Fanning Corporation under the names Fancorsil SLA and Fancorsil LIM1, and by the company Phoenix under the name Pecosil.

These silicones are especially described in U.S. Pat. Nos. 5,070,171, 5,149,765, 5,093,452 and 5,091,493.

Oxyalkylenated silicones corresponding to the general formula (II) or (III) are preferably used. More particularly, these formulae satisfy at least one, and preferably all, of the following conditions:

c is equal to 2 or 3, $R_1$ denotes a methyl radical, $R_5$ represents a hydrogen atom, a methyl radical or a $C_{12}$-$C_{22}$ acyl radical, a ranges from 2 to 25 and more particularly from 2 to 20, b is equal to 0, n ranges from 0 to 100, p ranges from 1 to 20.

Even more preferentially, the oxyalkylenated silicone(s) according to the invention are chosen from the non-amino oxyethylenated silicones preferably of formula (II) in which:

$R_2$, which may be identical or different, represents a radical $-C_cH_{2c}-O-(C_2H_4O)_a(C_3H_6O)_b-R_5$, c is equal to 2 or 3, $R_1$ denotes a methyl radical, $R_5$ represents a hydrogen atom, a ranges from 2 to 25 and more particularly from 2 to 20, b is equal to 0, n ranges from 0 to 100, p ranges from 1 to 20.

The oxyalkylenated silicones according to the invention may also be chosen from the silicones of formula (V) below:

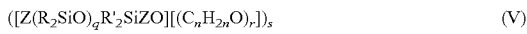

$$([Z(R_2SiO)_qR'_2SiZO][(C_nH_{2n}O)_r])_s \quad (V)$$

in which formula (V):

$R_2$ and $R'_2$, which may be identical or different, represent a monovalent hydrocarbon-based radical, n is an integer ranging from 2 to 4, q is a number greater than or equal to 4, preferably between 4 and 200 and even more particularly between 4 and 100, r is a number greater than or equal to 4, preferably between 4 and 200 and even more particularly between 5 and 100, s is a number greater than or equal to 4, preferably between 4 and 1000 and even more particularly between 5 and 300, Z represents a divalent organic group linked to the adjacent silicon atom via a carbon-silicon bond and to a polyoxyalkylene block via an oxygen atom, the average molecular weight of each siloxane block is between about 400 and about 10 000, that of each polyoxyalkylene block being between about 300 and about 10 000, the siloxane blocks represent from about 10% to about 95% by weight of the block copolymer, the number-average molecular weight of the block copolymer ranges from 2500 to 1 000 000, preferably between 3000 and 200 000 and even more particularly between 6000 and 100 000.

$R_2$ and $R'_2$ are preferably chosen from the group comprising linear or branched alkyl radicals, for instance methyl, ethyl, propyl, butyl, pentyl, hexyl, octyl, decyl and dodecyl radicals, aryl radicals, for instance phenyl and naphthyl, aralkyl or alkylaryl radicals, for instance benzyl and phenylethyl, and tolyl and xylyl radicals.

Z is preferably —R"—, —R"—CO—, —R"—NHCO—, —R"—NH—CO—NH—R'"— or —R"—OCONH—R'"—NHCO—, in which R" is a linear or branched $C_1$-$C_6$ divalent alkylene group, for instance ethylene, propylene or butylene, and R'" is a divalent alkylene group or a divalent arylene group, for instance —$C_6H_4$—, —$C_6H_4$—$C_6H_4$—, —$C_6H_4$—$CH_2$—$C_6H_4$— or —$C_6H_4$—$C(CH_3)_2C_6H_4$—.

Even more preferentially, Z represents a divalent alkylene radical, more particularly a linear or branched —$C_3H_6$— radical or a —$C_4H_8$— radical.

The preparation of the block copolymers used in the context of the present invention is described in European patent application EP 0 492 657 A1, the teaching of which is included in the present description.

Such products are sold, for example, under the name Silicone Fluid FZ-2172 by the company OSI.

Preferably, the oxyalkylenated silicone(s) of the first composition represent from 0.01% to 10% by weight, preferably from 0.05% to 5% by weight and more preferentially from 0.1% to 2% by weight relative to the total weight of the first composition.

As described previously, the first composition and the second composition that may be used in the process according to the invention also comprise one or more cationic surfactants, which are preferably non-silicone surfactants.

The term "cationic surfactant" means a surfactant that is positively charged when it is contained in a composition that may be used according to the invention. This surfactant may bear one or more positive permanent charges or may contain one or more cationizable functions within a composition that may be used according to the invention.

The first cationic surfactant(s) of the first composition and the second cationic surfactant(s) of the second composition are preferably chosen, independently from one another, from primary, secondary or tertiary fatty amines, which are optionally polyoxyalkylenated, or salts thereof, and quaternary ammonium salts, and mixtures thereof.

The fatty amines generally comprise at least one $C_8$-$C_{30}$ hydrocarbon-based chain.

Examples of quaternary ammonium salts that may especially be mentioned include:

those corresponding to the following general formula (VI):

in which formula (VI):

the groups $R_8$ to $R_{11}$, which may be identical or different, represent a linear or branched aliphatic group comprising from 1 to 30 carbon atoms, or an aromatic group such as aryl or alkylaryl, at least one of the groups $R_8$ to $R_{11}$ denoting a linear or branched aliphatic radical comprising from 8 to 30 carbon atoms, preferably from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_1$-$C_{30}$ alkoxy, ($C_2$-$C_6$) polyoxyalkylene, $C_1$-$C_{30}$ alkylamide, ($C_{12}$-$C_{22}$)alkylamido($C_2$-$C_6$)alkyl, ($C_{12}$-$C_{22}$)alkyl acetate, and $C_1$-$C_{30}$ hydroxyalkyl groups;

$X^-$ is an anion chosen from the group of halides, phosphates, acetates, lactates, ($C_1$-$C_4$)alkyl sulfates, ($C_1$-$C_4$)alkylsulfonates or ($C_1$-$C_4$)alkylarylsulfonates.

Among the quaternary ammonium salts of formula (VI), the ones that are preferred are, on the one hand, tetraalkylammonium salts, for instance dialkyldimethylammonium or alkyltrimethylammonium salts in which the alkyl group comprises approximately from 12 to 22 carbon atoms, in particular behenyltrimethylammonium, distearyldimethylammonium, cetyltrimethylammonium or benzyldimethylstearylammonium salts, or, on the other hand, the palmitylamidopropyltrimethylammonium or stearamidopropyltrimethylammonium salts, the stearamidopropyldimethylcetearylammonium salts, or the stearamidopropyldimethyl(myristyl acetate)ammonium salts sold under the name Ceraphyl® 70 by the company Van Dyk. It is preferred in particular to use the chloride salts of these compounds.

quaternary ammonium salts of imidazoline, for instance those of formula (VII) below:

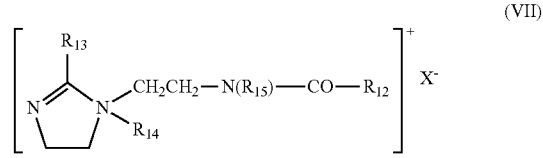

in which formula (VII):

$R_{12}$ represents an alkenyl or alkyl group comprising from 8 to 30 carbon atoms, for example derived from tallow fatty acids, $R_{13}$ represents a hydrogen atom, a $C_1$-$C_4$ alkyl group or an alkenyl or alkyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkylsulfonates or alkylarylsulfonates in which the alkyl and aryl groups preferably comprise, respectively, from 1 to 20 carbon atoms and from 6 to 30 carbon atoms.

Preferably, $R_{12}$ and $R_{13}$ denote a mixture of alkenyl or alkyl groups comprising from 12 to 21 carbon atoms, for example derived from tallow fatty acids, $R_{14}$ denotes a methyl group and $R_{15}$ denotes a hydrogen atom.

Such a product is sold, for example, under the name Rewoquat® W 75 by the company Rewo;

diquaternary or triquaternary ammonium salts of formula (VIII):

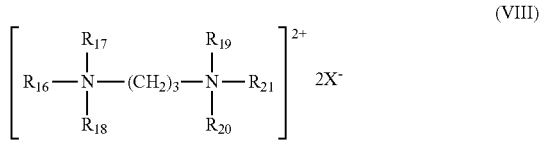

in which formula (VIII):

$R_{16}$ denotes an alkyl group comprising approximately from 16 to 30 carbon atoms, which is optionally hydroxylated and/or optionally interrupted with one or more oxygen atoms, $R_{17}$ denotes hydrogen, an alkyl group comprising from 1 to 4 carbon atoms or a group $—(CH_2)_3—N(R_{16a})(R_{17a})(R_{18a})$; $R_{16a}$, $R_{17a}$ and $R_{18a}$, which may be identical or different, denoting hydrogen or an alkyl group comprising from 1 to 4 carbon atoms, $R_{18}$, $R_{19}$, $R_{20}$ and $R_{21}$, which may be identical or different, denote hydrogen or an alkyl group comprising from 1 to 4 carbon atoms, and $X^-$ is an anion, chosen especially from the group of halides, acetates, phosphates, nitrates, $(C_1$-$C_4)$alkyl sulfates, $(C_1$-$C_4)$alkylsulfonates and $(C_1$-$C_4)$alkylarylsulfonates, in particular methyl sulfate and ethyl sulfate.

Such compounds are, for example, Finquat CT-P (Quaternium 89) and Finquat CT (Quaternium 75), sold by the company Finetex.

quaternary ammonium salts containing one or more ester functions of formula (IX) below:

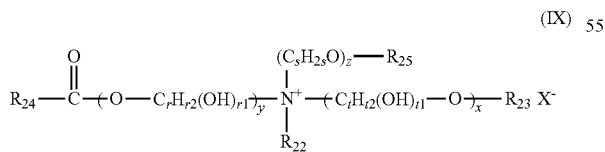

in which formula (IX):

$R_{22}$ is chosen from $C_1$-$C_6$ alkyl groups and $C_1$-$C_6$ hydroxyalkyl or dihydroxyalkyl groups, $R_{23}$ is chosen from the group $R_{26}—C(=O)—$; linear or branched, saturated or unsaturated $C_1$-$C_{22}$ hydrocarbon-based groups $R_{27}$; and a hydrogen atom, $R_{25}$ is chosen from the group $R_{28}—C(=O)—$; linear or branched, saturated or unsaturated $C_1$-$C_6$ hydrocarbon-based groups $R_{29}$; and a hydrogen atom, $R_{24}$, $R_{26}$ and $R_{28}$, which may be identical or different, are chosen from linear or branched, saturated or unsaturated $C_7$-$C_{21}$ hydrocarbon-based groups, r, s and t, which may be identical or different, are integers ranging from 2 to 6, r1 and t1, which may be identical or different, are equal to 0 or 1, r2 and t2, which may be identical or different, are integers such that r2+r1=2r and t1+t2=2t, y is an integer ranging from 1 to 10, x and z, which may be identical or different, are integers ranging from 0 to 10, it being understood that the sum x+y+z is from 1 to 15, $X^-$ is an anion, with the proviso that when x=0 then $R_{23}$ denotes $R_{27}$ and that when z=0 then $R_{25}$ denotes $R_{29}$.

The alkyl groups $R_{22}$ may be linear or branched, preferably linear. Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is a hydrocarbon-based group $R_{27}$, it may comprise from 12 to 22 carbon atoms, or else may comprise from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched $C_{11}$-$C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide, preferably chloride, bromide or iodide, a $(C_1$-$C_4)$alkyl sulfate, a $(C_1$-$C_4)$alkylsulfonate or a $(C_1$-$C_4)$alkylarylsulfonate, a methanesulfonate, a phosphate, a nitrate, a tosylate, an anion derived from an organic acid such as an acetate or a lactate or any other anion that is compatible with the ammonium bearing an ester function. The anion $X^-$ is more particularly a chloride, a methyl sulfate or an ethyl sulfate.

Use is more particularly made, according to the invention, of the ammonium salts of formula (IX) in which:

$R_{22}$ denotes a methyl or ethyl group, x and y are equal to 1, z is equal to 0 or 1, r, s and t are equal to 2, r2 and t2 are equal to 4, r1 and t1 are equal to 0, $R_{23}$ is chosen from the group $R_{26}—C(=O)—$, methyl, ethyl or $C_{14}$-$C_{22}$ hydrocarbon-based groups, and a hydrogen atom, $R_{25}$ is chosen from the group $R_{28}—C(=O)—$; a hydrogen atom, $R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon-based groups are linear.

Mention may be made, among the compounds of formula (IX), of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium salts, in particular the chloride or the methyl sulfate, and mixtures thereof. The acyl groups preferably contain 14 to 18 carbon atoms and are derived more particularly from a plant oil such as palm oil or sunflower oil. When the compound contains several acyl groups, these groups may be identical or different.

These products are obtained, for example, by direct esterification of triethanolamine, triisopropanolamine, alkyldiethanolamine or alkyldiisopropanolamine, which are optionally oxyalkylenated, with fatty acids or with fatty acid mixtures especially of plant or animal origin, or by transesterification of the methyl esters thereof. This esterification may be followed by a quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin. Such compounds are sold, for example, under the names Dehyquart® by the company Henkel, Stepanquat® by the company Stepan, Noxamium® by the company Ceca or Rewoquat® WE 18 by the company Evonik.

The first composition and the second that may be used according to the invention may contain, for example, a mixture of quaternary ammonium monoester, diester and triester salts with a weight majority of diester salts. Use may also be made of the ammonium salts containing at least one ester function that are described in U.S. Pat. Nos. 4,874,554 and 4,137,180. Use may also be made of behenoylhydroxypropyltrimethylammonium chloride, for example, sold by the company Kao under the name Quartamin BTC 131.

Preferably, the ammonium salts containing at least one ester function contain two ester functions.

The first cationic surfactant(s) of the first composition and the second cationic surfactant(s) of the second composition may also be chosen, independently from one another, from a mixture of the cationic surfactants of formulae (VI) to (IX) above.

Preferably, the first cationic surfactant(s) of the first composition and/or the second cationic surfactant(s) of the second composition are chosen from those of formula (VI) or (IX) and mixtures of these compounds, and more preferentially from those of formula (VI) and mixtures of these compounds.

In a particularly preferred manner, the first cationic surfactant(s) of the first composition and the second cationic surfactant(s) of the second composition are chosen, independently from one another, from cetyltrimethylammonium, behenyltrimethylammonium and dipalmitoylethylhydroxyethylmethylammonium salts and mixtures thereof; and in particular from cetyltrimethylammonium and behenyltrimethylammonium salts and mixtures thereof.

In a most particularly preferred manner, the first cationic surfactant(s) of the first composition and the second cationic surfactant(s) of the second composition are chosen, independently from one another, from behenyltrimethylammonium chloride or methosulfate, cetyltrimethylammonium chloride or methosulfate, dipalmitoylethylhydroxyethylmethylammonium chloride or methosulfate, and mixtures thereof, and in particular from behenyltrimethylammonium chloride or methosulfate, and cetyltrimethylammonium chloride or methosulfate, and mixtures thereof.

Advantageously, the first cationic surfactant(s) of the first composition represent a total content of from 0.05% to 15% by weight, preferably from 0.1% to 10% by weight and more preferentially from 1% to 5% by weight relative to the total weight of the first composition.

Advantageously, the second cationic surfactant(s) of the second composition represent a total content of from 0.05% to 10% by weight, preferably from 0.1% to 5% by weight, and more preferentially from 0.5% to 2% by weight, relative to the total weight of the second composition.

As indicated previously, the second composition that may be used in the process according to the invention comprises water.

Advantageously, the second composition comprises at least 15% by weight, preferably comprises at least 50% by weight, more preferentially from 50% to 99.5% by weight, in particular from 70% to 99.5% and better still from 80% to 99.5% by weight of water, relative to the total weight of the second composition.

The first and the second compositions that may be used in the process according to the invention may each and/or both also comprise one or more non-silicone fatty substances.

The term "fatty substance" means an organic compound that is insoluble in water at room temperature (25° C.) and at atmospheric pressure (1 atm), i.e. which has a solubility of less than 5% by weight, preferably less than 1% by weight. They are generally soluble, under the same temperature and pressure conditions, in organic solvents such as chloroform, ethanol, benzene, liquid petroleum jelly or decamethylcyclopentasiloxane.

The term "non-silicone fatty substance" means a fatty substance whose structure does not comprise any silicon atoms, and which therefore especially does not comprise any siloxane groups. They generally bear in their structure a hydrocarbon-based chain comprising at least 6 carbon atoms. Advantageously, they are not oxyalkylenated and do not contain any —COOH functions.

The non-silicone fatty substance(s) that may be used according to the invention may be liquid or non-liquid at room temperature and at atmospheric pressure.

The liquid fatty substances that may be used in the invention preferably have a viscosity of less than or equal to 2 Pa·s, better still less than or equal to 1 Pa·s and even better still less than or equal to 0.1 Pa·s at a temperature of 25° C. and at a shear rate of 1 s$^{-1}$.

The liquid fatty substances that may be used according to the invention may be chosen especially from liquid hydrocarbons, liquid fatty alcohols, liquid fatty esters and liquid fatty acids, and mixtures of these compounds.

The term "liquid hydrocarbon" means a hydrocarbon composed solely of carbon and hydrogen atoms, which is liquid at ordinary temperature (25° C.) and at atmospheric pressure (760 mmHg, i.e. 1.013×10$^5$ Pa).

More particularly, the liquid hydrocarbons are chosen from:
- linear or branched, optionally cyclic, $C_6$-$C_{16}$ alkanes. Examples that may be mentioned include hexane, undecane, dodecane, tridecane, and isoparaffins, for instance isohexadecane, isododecane and isodecane;
- linear or branched hydrocarbons of mineral, animal or synthetic origin with more than 16 carbon atoms, such as liquid paraffins and derivatives thereof, petroleum jelly, liquid petroleum jelly, polydecenes, hydrogenated polyisobutene such as the product sold under the brand name Parleam® by the company NOF Corporation, and squalane.

Preferably, the liquid hydrocarbon(s) are chosen from liquid paraffins, isoparaffins, liquid petroleum jelly, undecane, tridecane and isododecane, and mixtures thereof.

In a most particularly preferred variant, the liquid hydrocarbon(s) are chosen from liquid petroleum jelly, isoparaffins, isododecane and a mixture of undecane and tridecane.

The term "liquid fatty alcohol" means a non-glycerolated and non-oxyalkylenated fatty alcohol, which is liquid at ordinary temperature (25° C.) and at atmospheric pressure (760 mmHg, i.e. $1.013 \times 10^5$ Pa). Preferably, the liquid fatty alcohols of the invention comprise from 8 to 30 carbon atoms, especially from 10 to 24 carbon atoms, and may be saturated or unsaturated.

The saturated liquid fatty alcohols are preferably branched. They may optionally comprise in their structure at least one aromatic or non-aromatic ring, which is preferably acyclic.

More particularly, the saturated liquid fatty alcohols of the invention are chosen from octyldodecanol, 2-decyltetradecanol, isostearyl alcohol and 2-hexyldecanol.

Octyldodecanol and 2-decyltetradecanol are most particularly preferred.

The unsaturated liquid fatty alcohols contain in their structure at least one double or triple bond, and preferably one or more double bonds. When several double bonds are present, there are preferably 2 or 3 of them, and they may be conjugated or unconjugated.

These unsaturated fatty alcohols may be linear or branched.

They may optionally comprise in their structure at least one aromatic or non-aromatic ring. They are preferably acyclic.

More particularly, the unsaturated liquid fatty alcohols that may be used in the invention are chosen from oleyl alcohol, linoleyl alcohol, linolenyl alcohol and undecylenyl alcohol.

Oleyl alcohol is most particularly preferred.

The term "liquid fatty ester" means an ester derived from a fatty acid and/or from a fatty alcohol, which is liquid at ordinary temperature (25° C.) and at atmospheric pressure (760 mmHg; i.e. $1.013 \times 10^5$ Pa).

More particularly, the liquid esters are chosen from esters of saturated or unsaturated, linear or branched $C_1$-$C_{26}$ aliphatic mono- or polyacids, which are optionally hydroxylated, and from saturated or unsaturated, linear or branched $C_1$-$C_{26}$ aliphatic mono- or polyalcohols, the total number of carbon atoms in the esters being greater than or equal to 10.

Preferably, for the esters of monoalcohols, at least one from among the alcohol and the acid from which the esters of the invention are derived is branched.

Among the monoesters of monoacids and of monoalcohols, mention may be made of alkyl palmitates, in particular of $C_1$-$C_{18}$, especially ethyl palmitate and isopropyl palmitate, alkyl myristates in particular of $C_1$-$C_{18}$, such as isopropyl myristate or ethyl myristate, alkyl stearates, in particular of $C_1$-$C_{18}$, especially isocetyl stearate, 2-ethylhexyl isononanoate, isodecyl neopentanoate and isostearyl neopentanoate.

Esters of optionally hydroxylated $C_3$-$C_{22}$ dicarboxylic or tricarboxylic acids and of $C_1$-$C_{22}$ alcohols and esters of optionally hydroxylated monocarboxylic, dicarboxylic or tricarboxylic acids and of $C_4$-$C_{26}$ dihydroxy, trihydroxy, tetrahydroxy or pentahydroxy non-sugar alcohols may also be used.

Mention may be made especially of diethyl sebacate, diisopropyl sebacate, diisopropyl adipate, di-n-propyl adipate, dioctyl adipate, diisostearyl adipate, dioctyl maleate, glyceryl undecylenate, octyldodecyl stearoyl stearate, pentaerythrityl monoricinoleate, pentaerythrityl tetraisononanoate, pentaerythrityl tetrapelargonate, pentaerythrityl tetraisostearate, pentaerythrityl tetraoctanoate, propylene glycol dicaprylate, propylene glycol dicaprate, tridecyl erucate, triisopropyl citrate, triisostearyl citrate, glyceryl trilactate, glyceryl trioctanoate, trioctyldodecyl citrate, trioleyl citrate, propylene glycol dioctanoate, neopentyl glycol diheptanoate, diethylene glycol diisononanoate, polyethylene glycol distearates, and alkyl malates, especially ($C_6$-$C_{18}$)alkyl malates, in particular bis($C_{12}$-$C_{13}$)alkyl malate. Among the esters mentioned above, use is preferentially made of ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, propylene glycol dicaprylate, butyl stearate, isobutyl stearate; dioctyl malate, hexyl laurate, 2-hexyldecyl laurate, isononyl isononanoate, cetyl octanoate and bis($C_{12}$-$C_{13}$)alkyl malate. Among the liquid fatty esters, use may be made of sugar esters and diesters of $C_6$-$C_{30}$ and preferably $C_{12}$-$C_{22}$ fatty acids.

The term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Preferably, these said sugars are chosen from sucrose, glucose, galactose, ribose, fucose, maltose, fructose, mannose, arabinose, xylose and lactose, and derivatives thereof, especially alkyl derivatives, such as methyl derivatives, for instance methylglucose.

The sugar and fatty acid esters may be chosen especially from the group comprising the esters or mixtures of esters of sugars described previously and of linear or branched, saturated or unsaturated $C_6$-$C_{30}$ and preferably $C_{12}$-$C_{22}$ fatty acids.

If they are unsaturated, these compounds may comprise one to three conjugated or unconjugated carbon-carbon double bonds.

The esters according to this variant may also be chosen from mono-, di-, tri- and tetraesters, and polyesters, and mixtures thereof.

These esters may be, for example, oleates, laurates, palmitates, myristates, behenates, cocoates, stearates, linoleates, linolenates, caprates and arachidonates, and mixtures thereof, such as, especially, oleopalmitate, oleostearate or palmitostearate mixed esters.

More particularly, use is made of monoesters and diesters and especially of sucrose, glucose or methylglucose mono- or dioleates, stearates, behenates, oleopalmitates, linoleates, linolenates or oleostearates, or alternatively of methylglucose dioleate (Glucate® DO).

Among the sugar esters, use may be made of pentaerythrityl esters, preferably pentaerythrityl tetraisostearate, pentaerythrityl tetraoctanoate, and caprylic and capric acid hexaesters as a mixture with dipentaerythritol.

Among the natural or synthetic monoacid, diacid or triacid esters of glycerol, use may be made of plant oils or synthetic oils.

More particularly, said plant oil(s) or synthetic oil(s) are chosen from triglyceride oils of plant or synthetic origin, such as liquid fatty acid triglycerides containing from 6 to 30 carbon atoms, for instance heptanoic or octanoic acid triglycerides, or alternatively, for example, sesame oil, soybean oil, coffee oil, safflower oil, borage oil, sunflower oil, olive oil, apricot kernel oil, camellia oil, bambara pea oil, avocado oil, mango oil, rice bran oil, cottonseed oil, rose oil, kiwi seed oil, sea buckthorn pulp oil, blueberry seed oil, poppy seed oil, orange pip oil, sweet almond oil, palm oil, coconut oil, vernonia oil, marjoram oil, baobab oil, rapeseed oil, ximenia oil, pracaxi oil, caprylic/capric acid triglycerides such as those sold by the company Stéarineries Dubois or those sold under the names Miglyol® 810, 812 and 818 by the company Dynamit Nobel, jojoba oil and shea butter oil.

As liquid esters that may be used according to the invention, use is preferably made of triglycerides of plant origin, in particular oils chosen from avocado oil, olive oil, camellia oil and apricot kernel oil, and mixtures thereof, and $C_4$-$C_{22}$ dicarboxylic or tricarboxylic acid esters of $C_1$-$C_{22}$ alcohols, in particular 1,3-propanediol dicaprylate.

The term "fatty acid" means a non-salified fatty acid, i.e. the fatty acid must not be in the form of a generally soluble soap, i.e. it must not be salified with a base.

More particularly, the liquid fatty acids that may be used according to the invention are chosen from the acids of formula RCOOH, in which R is a saturated or unsaturated, linear or branched radical preferably comprising from 7 to 39 carbon atoms.

Preferably, R is a $C_7$-$C_{29}$ alkyl or $C_7$-$C_{29}$ alkenyl group and better still a $C_{12}$-$C_{24}$ alkyl or $C_{12}$-$C_{24}$ alkenyl group. R may be substituted with one or more hydroxyl groups and/or one or more carboxyl groups.

Preferentially, the liquid fatty acid(s) are chosen from oleic acid, linoleic acid and isostearic acid.

The fatty substance(s) that may be used according to the invention may also be chosen from fatty substances that are not liquid at room temperature (25° C.) and at atmospheric pressure (760 mmHg, i.e. $1.013 \times 10^5$ Pa).

The term "non-liquid fatty substance" preferably means a solid compound or a compound with a viscosity of greater than 2 Pa·s at a temperature of 25° C. and at a shear rate of 1 $s^{-1}$.

More particularly, the non-silicone "non-liquid" fatty substances are chosen from fatty alcohols, fatty acid and/or fatty alcohol esters, non-silicone waxes, fatty amines and fatty ethers, which are non-liquid and preferably solid.

More particularly, the non-liquid fatty alcohols that may be used according to the invention are chosen from linear or branched, saturated or unsaturated alcohols comprising from 8 to 30 carbon atoms.

Examples that may preferably be mentioned include myristyl alcohol, cetyl alcohol, stearyl alcohol and a mixture thereof (especially cetylstearyl alcohol). Myristyl alcohol is more particularly used.

The non-liquid ester(s) of fatty acids and/or of fatty alcohols that may be used according to the invention are generally chosen from solid esters derived from $C_9$-$C_{26}$ fatty acids and from $C_9$-$C_{26}$ fatty alcohols.

Examples that may preferably be mentioned include octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate or stearyl myristate, and hexyl stearate.

The non-silicone wax(es) are chosen especially from carnauba wax, candelilla wax, esparto wax, paraffin wax, ozokerite, plant waxes, such as olive tree wax, rice wax, hydrogenated jojoba wax and absolute flower waxes, such as the blackcurrant blossom essential wax sold by Bertin (France), and animal waxes, such as beeswaxes or modified beeswaxes (cerabellina), and ceramides or analogues.

The ceramides or ceramide analogues, such as natural or synthetic glycoceramides, may be chosen from the compounds corresponding to formula (X) below:

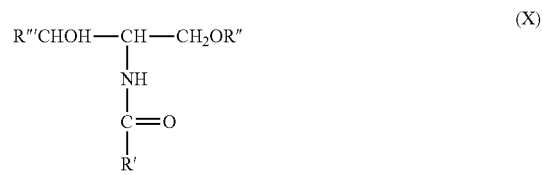

in which:
R' denotes a linear or branched, saturated or unsaturated alkyl radical derived from $C_{14}$-$C_{30}$ fatty acids, this radical possibly being substituted with a hydroxyl group in the alpha position, or a hydroxyl group in the omega position which is esterified with a saturated or unsaturated $C_{16}$-$C_{30}$ fatty acid;
R" denotes a hydrogen atom or a (glycosyl)$_n$, (galactosyl)$_m$ or sulfogalactosyl radical, in which n is an integer ranging from 1 to 4 and m is an integer ranging from 1 to 8;
R'" denotes a $C_{15}$-$C_{26}$ hydrocarbon-based radical, saturated or unsaturated in the alpha position, this radical possibly being substituted with one or more $C_1$-$C_{14}$ alkyl radicals;
it being understood that, in the case of natural ceramides or glycoceramides, R'" may also denote a $C_{15}$-$C_{26}$ alpha-hydroxyalkyl radical, the hydroxyl group being optionally esterified with a $C_{16}$-$C_{30}$ alpha-hydroxy acid.

The ceramides that are preferred in the context of the present invention are those described by Downing in Arch. Dermatol, Vol. 123, 1381-1384, 1987, or those described in French patent FR 2 673 179.

The ceramide(s) that are more particularly preferred according to the invention are the compounds for which R' denotes a saturated or unsaturated alkyl derived from $C_{16}$-$C_{22}$ fatty acids, R" denotes a hydrogen atom and R'" denotes a linear, saturated $C_{15}$ radical.

Preferentially, the following compounds may especially be chosen: N-linoleoyldihydrosphingosine, N-oleoyldihydrosphingosine, N-palmitoyldihydrosphingosine, N-stearoyldihydrosphingosine, N-behenoyldihydrosphingosine, and a mixture of these compounds.

Even more preferentially, the ceramides used are those for which R' denotes a saturated or unsaturated alkyl radical derived from fatty acids, R" denotes a galactosyl or sulfogalactosyl radical and R'" denotes a —CH═CH—(CH$_2$)$_{12}$—CH$_3$ group.

Other waxes or waxy starting materials that may be used according to the invention are especially marine waxes such as those sold by Sophim under the reference M82, and waxes of polyethylene or of polyolefins in general.

The non-liquid fatty ethers that may be used according to the invention are chosen from dialkyl ethers and especially dicetyl ether and distearyl ether, alone or as a mixture.

Preferentially, the non-silicone fatty substance(s) that may be used according to the invention are chosen from hydrocarbons, in particular linear or branched $C_6$-$C_{16}$ alkanes and linear or branched hydrocarbons of mineral, animal or synthetic origin, of more than 16 carbon atoms, such as liquid paraffins and derivatives thereof, petroleum jelly, liquid petroleum jelly; fatty acid esters, in particular oils of plant origin and $C_4$-$C_{22}$ dicarboxylic or tricarboxylic acid esters of $C_1$-$C_{22}$ alcohols, these esters being chosen more preferentially from triglycerides of plant origin, liquid fatty alcohols and solid fatty alcohols, and mixtures thereof.

When they are present in the first composition that may be used according to the process of the invention, the non-silicone fatty substance(s) generally represent from 1% to 50% by weight, preferably from 2% to 30% by weight and more preferentially from 10% to 30% by weight relative to the total weight of the first composition.

When they are present in the second composition that may be used according to the process of the invention, the non-silicone fatty substance(s) generally represent from 0.001% to 10% by weight, preferably from 0.01% to 1% by weight and more preferentially from 0.05% to 0.5% by weight relative to the total weight of the second composition.

In a most particularly preferred embodiment of the invention, the first composition comprises one or more non-silicone fatty substances, preferably chosen from $C_8$-$C_{28}$ and preferably $C_{10}$-$C_{24}$ fatty alcohols, and fatty esters preferentially chosen from ($C_6$-$C_{18}$)alkyl malates and in particular bis($C_{12}$-$C_{13}$)alkyl malate.

Preferably, in this embodiment, the first composition comprises at least one ($C_6$-$C_{18}$)alkyl malate, in particular bis($C_{12}$-$C_{13}$)alkyl malate.

Advantageously, the second composition that may be used in the process according to the invention may comprise one or more non-amino non-oxyalkylenated silicones.

The first and the second compositions that may be used in the process according to the invention may each and/or both also comprise one or more surfactants chosen from non-ionic, anionic and amphoteric or zwitterionic surfactants.

The first and the second compositions that may be used in the process according to the invention may each and/or both also comprise one or more organic solvents.

Preferably, the organic solvent(s) are chosen from $C_1$-$C_6$ non-aromatic alcohols such as ethyl alcohol or isopropyl alcohol, or aromatic alcohols such as benzyl alcohol and phenylethyl alcohol; polyos such as propylene glycol, butylene glycol or glycerol or polyol ethers, for instance ethylene glycol monomethyl, monoethyl or monobutyl ethers, propylene glycol and the ethers thereof, for instance propylene glycol monomethyl ether, butylene glycol, dipropylene glycol and also diethylene glycol alkyl ethers, for instance diethylene glycol monoethyl ether or monobutyl ether.

In a particularly preferred manner, the first composition that may be used in the process according to the invention comprises one or more organic solvents preferably chosen from ethyl alcohol and propylene glycol, and mixtures thereof.

When they are present in the first composition that may be used according to the process of the invention, the organic solvent(s) generally represent a total content of from 20% to 95% by weight, preferably from 45% to 85% by weight and more preferentially from 55% to 80% by weight relative to the total weight of the first composition.

When they are present in the second composition that may be used according to the process of the invention, the organic solvent(s) generally represent a total content of from 0.1% to 15% by weight and preferably from 1% to 10% by weight relative to the total weight of the second composition.

In a particular embodiment, the first and/or the second compositions that may be used according to the process of the invention may comprise one or more cationic polymers.

Preferably, in this particular embodiment, the second composition comprises one or more cationic polymers.

The term "cationic polymer" means any polymer comprising cationic groups and/or groups that can be ionized to cationic groups. Preferably, the cationic polymer is hydrophilic or amphiphilic. The preferred cationic polymers are chosen from those that contain units comprising primary, secondary, tertiary and/or quaternary amine groups that may either form part of the main polymer chain or may be borne by a side substituent directly connected thereto.

More particularly, the cationic polymers that may be used according to the present invention are chosen from polymers of polyamine, polyaminoamide and polyquaternary ammonium type, polyalkyleneimines and mixtures thereof.

The polymers of polyamine, polyaminoamide and polyquaternary ammonium type, that may be used in accordance with the present invention, and that may in particular be mentioned, are those described in French patents No. 2 505 348 or 2 542 997.

Among the cationic polymer(s) that may be used according to the invention, mention may be made of:

(1) quaternized or non-quaternized vinylpyrrolidone/dialkylaminoalkyl (meth)acrylate copolymers;

(2) polymers formed from piperazinyl units and divalent alkylene or hydroxyalkylene groups containing straight or branched chains, optionally interrupted with oxygen, sulfur or nitrogen atoms or with aromatic or heterocyclic rings, and also the oxidation and/or quaternization products of these polymers. Such polymers are described, in particular, in French patents 2162025 and 2280361;

(3) water-soluble polyaminoamides prepared in particular by polycondensation of an acidic compound with a polyamine; these polyaminoamides can be crosslinked by an epihalohydrin, a diepoxide, a dianhydride, an unsaturated dianhydride, a bisunsaturated derivative, a bishalohydrin, a bisazetidinium, a bishaloacyldiamine or an alkyl bishalide or alternatively by an oligomer resulting from the reaction of a difunctional compound reactive with respect to a bishalohydrin, a bisazetidinium, a bishaloacyldiamine, an alkyl bishalide, an epihalohydrin, a diepoxide or a bisunsaturated derivative; the crosslinking agent being used in proportions ranging from 0.025 to 0.35 mol per amine group of the polyaminoamide; these polyaminoamides can be alkylated or, if they comprise one or more tertiary amine functions, quaternized. Such polymers are described, in particular, in French patents 2,252,840 and 2,368,508;

(4) polyaminoamide derivatives resulting from the condensation of polyalkylene-polyamines with polycarboxylic acids, followed by alkylation with difunctional agents. Mention may be made, for example, of adipic acid/dialkylaminohydroxyalkyldialkylenetriamine polymers in which the alkyl group includes from 1 to 4 carbon atoms and preferably denotes methyl, ethyl or propyl. Such polymers are in particular described in French patent 1 583 363;

(5) the polymers obtained by reaction of a polyalkylene-polyamine containing two primary amine groups and at least one secondary amine group with a dicarboxylic acid chosen from diglycolic acid and saturated aliphatic dicarboxylic acids containing from 3 to 8 carbon atoms. The mole ratio between the polyalkylene-polyamine and the dicarboxylic acid is between 0.8:1 and 1.4:1; the resulting polyaminoamide is reacted with epichlorohydrin in a mole ratio of epichlorohydrin relative to the secondary amine group of the polyaminoamide of between 0.5:1 and 1.8:1. Such polymers are described in particular in U.S. Pat. Nos. 3,227,615 and 2,961,347;

(6) alkyldiallylamine or dialkyldiallylammonium cyclopolymers, such as homopolymers or copolymers including units corresponding to formula (XI) or (XII):

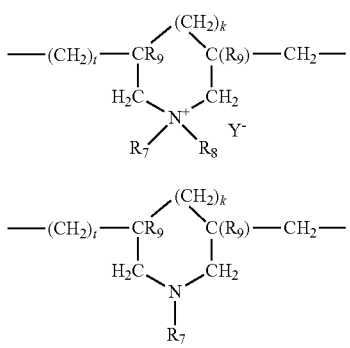

in which:
k and t are equal to 0 or 1, the sum k+t being equal to 1;
$R_9$ denotes a hydrogen atom or a methyl group;
$R_7$ and $R_8$, independently of each other, denote an alkyl group containing from 1 to 22 carbon atoms, a hydroxyalkyl group in which the alkyl group contains preferably 1 to 5 carbon atoms, a lower amidoalkyl group, or $R_7$ and $R_8$ may denote, together with the nitrogen atom to which they are attached, heterocyclic groups such as piperidyl or morpholinyl; and
$Y^-$ is an anion such as bromide, chloride, acetate, borate, citrate, tartrate, bisulfate, bisulfite, sulfate or phosphate.

Such polymers are especially described in French patent 2080759 and its certificate of addition 2190406.

Mention may be made, for example, of the diallyldimethylammonium chloride homopolymer sold under the name "Merquat® 100" by the company Nalco (Lubrizol), and the copolymers of diallyldimethylammonium chloride and of acrylamide.

(7) diquaternary ammonium polycondensates containing repeating units corresponding to formula (XIII):

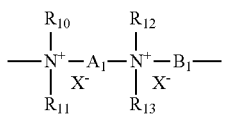

in which:
$R_{10}$, $R_{11}$, $R_{12}$ and $R_{13}$, which may be identical or different, represent aliphatic, alicyclic or arylaliphatic groups containing from 1 to 20 carbon atoms or lower hydroxyalkylaliphatic groups, or alternatively $R_{10}$, $R_{11}$, $R_{12}$ and $R_{13}$, together or separately, constitute, with the nitrogen atoms to which they are attached, heterocycles optionally containing a second heteroatom other than nitrogen, or alternatively $R_{10}$, $R_{11}$, $R_{12}$ and $R_{13}$ represent a linear or branched $C_1$ to $C_6$ alkyl group substituted with a nitrile, ester, acyl or amide group or a group —CO—O—R-D or —CO—NH—R-D where R is an alkylene group and D is a quaternary ammonium group;
$A_1$ and $B_1$ represent polymethylene groups containing from 2 to 20 carbon atoms, which may be linear or branched, saturated or unsaturated, and which may contain, linked to or inserted in the main chain, one or more aromatic rings, or one or more oxygen or sulfur atoms or sulfoxide, sulfone, disulfide, amino, alkylamino, hydroxyl, quaternary ammonium, ureido, amide or ester groups, and $X^-$ denotes an anion derived from a mineral or organic acid; $A_1$, $R_{10}$ and $R_{12}$ can form, with the two nitrogen atoms to which they are attached, a piperazine ring; in addition, if A denotes a linear or branched, saturated or unsaturated alkylene or hydroxyalkylene group, $B_1$ can also denote a —$(CH_2)_n$—CO-D-OC—$(CH_2)_n$— group, in which D denotes:

a) a glycol residue of formula: —O—Z—O—, where Z denotes a linear or branched hydrocarbon-based group or a group corresponding to one of the following formulae:

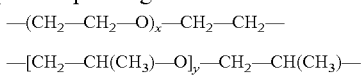

—[$CH_2$—$CH(CH_3)$—O$]_y$—$CH_2$—$CH(CH_3)$— where x and y denote an integer from 1 to 4, representing a defined and unique degree of polymerization or any number from 1 to 4 representing an average degree of polymerization;

b) a bis-secondary diamine residue, such as a piperazine derivative;

c) a bis-primary diamine residue of formula: —NH—Y—NH—, where Y denotes a linear or branched hydrocarbon-based group, or alternatively the divalent group

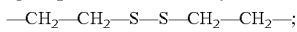

d) a ureylene group of formula: —NH—CO—NH—.

Preferably, $X^-$ is an anion, such as chloride or bromide.

These polymers have a number-average molecular mass generally between 1000 and 100 000 g/mol.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Use may more particularly be made of polymers that are formed from repeating units corresponding to formula (XIV):

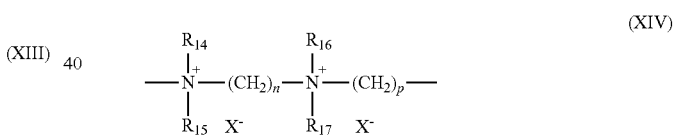

in which:
$R_{14}$, $R_{15}$, $R_{16}$ and $R_{17}$, which may be identical or different, each denote an alkyl or hydroxyalkyl group containing from 1 to 4 carbon atoms approximately,
n and p are integers ranging from 2 to 20 approximately, and
$X^-$ is an anion derived from a mineral or organic acid.

A compound of formula (XIV) that is particularly preferred is the one for which $R_{14}$, $R_{15}$, $R_{16}$ and $R_{17}$ represent a methyl group and n=3, p=6 and X=Cl, which is known as Hexadimethrine chloride according to the INCI (CTFA) nomenclature.

(8) polyquaternary ammonium polycondensates composed of units of formula (XV):

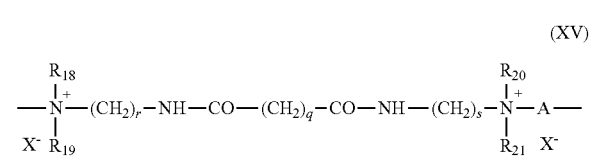

in which:
$R_{18}$, $R_{19}$, $R_{20}$ and $R_{21}$, which may be identical or different, represent a hydrogen atom or a methyl, ethyl, propyl, β-hydroxyethyl, β-hydroxypropyl or —CH$_2$CH$_2$(OCH$_2$CH$_2$)$_p$OH group, where p is equal to 0 or to an integer of between 1 and 6, with the proviso that $R_{18}$, $R_{19}$, $R_{20}$ and $R_{21}$ do not simultaneously represent a hydrogen atom,
r and s, which may be identical or different, are integers between 1 and 6,
q is equal to 0 or to an integer between 1 and 34,
X denotes a halogen atom, and
A denotes a dihalide group or preferably represents —CH$_2$—CH$_2$—O—CH$_2$—CH$_2$—.

Such compounds are especially described in patent application EP-A-122 324.

Among these, mention may be made, for example, of the products Mirapol® A 15, Mirapol® AD1, Mirapol® AZ1 and Mirapol® 175, sold by the company Miranol.

(9) homopolymers or copolymers derived from acrylic or methacrylic acids and comprising units (XVI), (XVII) and/or (XVIII):

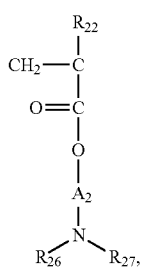

(XVI)

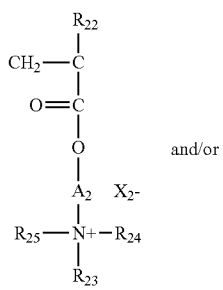

and/or (XVII)

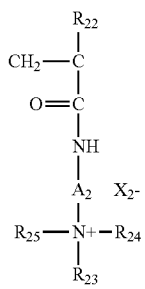

(XVIII)

in which:
$R_{22}$ independently denotes H or CH$_3$,
$A_2$ independently denotes a linear or branched alkyl group of 1 to 6 carbon atoms or a hydroxyalkyl group of 1 to 4 carbon atoms,
$R_{23}$, $R_{24}$, $R_{25}$, which may be identical or different, independently denote an alkyl group of 1 to 18 carbon atoms or a benzyl group,
$R_{26}$ and $R_{27}$ represent a hydrogen atom or an alkyl group of 1 to 6 carbon atoms, and
$X_2^-$ denotes an anion, for example methosulfate or halide, such as chloride or bromide.

The comonomer(s) that may be used for preparing the corresponding copolymers belong to the family of acrylamides, methacrylamides, diacetoneacrylamides, acrylamides and methacrylamides substituted on the nitrogen with lower alkyls, alkyl esters, acrylic or methacrylic acids, vinylpyrrolidone or vinyl esters.

(10) quaternary polymers of vinylpyrrolidone and of vinylimidazole;

(11) crosslinked polymers of methacryloyloxy(C$_1$-C$_4$)alkyltri(C$_1$-C$_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with an olefinically unsaturated compound, in particular methylenebisacrylamide;

(12) mixtures thereof.

Other cationic polymers that may be used in the context of the invention are polyalkyleneimines, in particular polyethyleneimines, polymers containing vinylpyridine or vinylpyridinium units, condensates of polyamines and of epichlorohydrin, polyquaternary ureylenes and chitin derivatives.

Among all the cationic polymers that may be used in the context of the present invention, the ones preferably used are those chosen from families (6), (7), (8), (9) and (11), as defined above, and more preferentially those chosen from family (7) as defined above.

When the first and/or the second composition that may be used in the process of the invention comprise one or more total cationic polymers, the total cationic polymer content is between 0.01% and 5% by weight, preferably between 0.05% and 3% by weight and more preferentially between 0.1% and 2% by weight relative to the total weight of the composition containing them.

The pH of the first composition that may be used in the process of the invention is generally between 2 and 7, preferably between 2.5 and 6, better still between 3 and 5.5 and preferentially between 3.5 and 5.

The pH of the second composition that may be used in the process of the invention is generally between 1 and 7, preferably between 2 and 6, better still between 2.5 and 5 and preferentially between 3 and 4.5.

The pH of the first and second compositions that may be used in the process of the invention may be adjusted and/or stabilized by means of basifying agents and/or acidifying agents that are well known to those skilled in the art.

Basifying agents that may especially be mentioned include aqueous ammonia, alkali metal carbonates or bicarbonates, organic amines with a pKb at 25° C. of less than 12, in particular less than 10 and even more advantageously less than 6; among the salts of the amines mentioned previously with acids such as carbonic acid or hydrochloric acid, it should be noted that it is the pKb corresponding to the function of highest basicity.

Preferably, the amines are chosen from alkanolamines, in particular comprising a primary, secondary or tertiary amine function, and one or more linear or branched C$_1$-C$_8$ alkyl groups bearing one or more hydroxyl radicals; from oxyethylenated and/or oxypropylenated ethylenediamines, and from amino acids and compounds having the following formula:

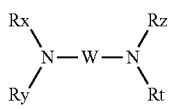

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical.

Acidifying agents that may especially be mentioned include hydrochloric acid, (ortho)phosphoric acid, sulfuric acid, boric acid, and also carboxylic acids, for instance acetic acid, lactic acid or citric acid, or sulfonic acids.

The first and second compositions that may be used in the process according to the invention may also contain additives such as natural or synthetic, anionic, amphoteric or zwitterionic or nonionic, associative or non-associative polymers, non-polymeric thickeners such as electrolytes, sugars, nacreous agents, opacifiers, sunscreens, vitamins or provitamins, fragrances, organic or mineral particles, or preserving agents.

A person skilled in the art will take care to select the optional additives and the amount thereof such that they do not harm the properties of the compositions that may be used in the process of the present invention.

These additives may be present in the compositions that may be used in the process according to the invention in an amount ranging from 0 to 50% by weight relative to the total weight of the composition containing them.

In one particular embodiment of the invention, the second composition comprises one or more vitamins.

In another particular embodiment of the invention, the second composition comprises one or more cationic polymers.

In this other particular embodiment of the invention, the cationic polymer(s) are preferably chosen from those mentioned above.

The first and second compositions that may be used in the process according to the invention are generally transparent.

The first and second compositions that may be used in the process according to the invention are generally liquid.

As described previously, the process according to the invention comprises a step of mixing of the first and second compositions as described above, so as to obtain a final cosmetic composition.

Preferably, the process according to the invention comprises a step of a single mixing of the first and second compositions as described above, so as to obtain a final cosmetic composition.

In the process according to the invention, the first and the second composition are generally mixed in a first composition/second composition weight ratio ranging from 0.2 to 5, preferably ranging from 0.3 to 3, more preferentially ranging from 0.5 to 1.5, and in particular the weight ratio is equal to 1/1.

In a particular embodiment of the process according to the invention, the mixing step is performed just before the application step, preferably less than two hours before, more preferentially less than one hour before and better still less than 15 minutes before the application step.

The final cosmetic composition obtained is generally opaque and has a thickened texture.

This texture makes it possible in particular to facilitate the application of the final composition to the keratin fibres.

Thus, the process according to the invention then comprises a step of applying the final cosmetic composition to the keratin fibres.

Preferably, once the final cosmetic composition has been spread, it is left on the keratin fibres for a time ranging from 2 to 15 minutes.

The final cosmetic composition may especially be applied before and/or after shampooing, dyeing, especially oxidation dyeing, permanent-waving, relaxing or any other hair treatment.

The composition may then be optionally rinsed out after application, preferably rinsed out.

A subject of the present invention is also a kit comprising at least two compartments:
 a first compartment comprising a first composition as defined above,
 a second compartment comprising a second composition as defined above.

Thus, each of the compositions is packaged separately, in particular in a bottle or a pump-dispenser bottle, and the two compartments may be separate or grouped together, preferably grouped together.

At the time of the cosmetic treatment, the user mixes at least said first composition with said second composition, for example in a suitable container, preferably in the weight ratio as indicated above.

The final cosmetic composition obtained is then ready to be applied to the keratin fibres.

Finally, a subject of the invention is a cosmetic composition for the cosmetic treatment of keratin fibres, comprising:
 i) one or more non-amino oxyalkylenated and preferably non-amino oxyethylenated silicones,
 ii) one or more first cationic surfactants,
 iii) one or more second cationic surfactants different from the cationic surfactants (ii),
 iv) water.

Preferably, the composition according to the invention is the final cosmetic composition resulting from the mixing of the first and the second compositions that may be used in the process according to the invention as described above.

Thus, preferably, the cosmetic composition according to the invention has one or more of the characteristics of the first and second compositions as described above, especially as regards the non-amino oxyalkylenated silicone(s) of the first composition, the first cationic surfactant(s) of the first composition, and the second cationic surfactant(s) of the second composition.

Preferably, the non-amino oxyalkylenated silicone(s) of the cosmetic composition according to the invention represent from 0.001% to 8.5% by weight, preferably from 0.008% to 4.5% by weight and more preferentially from 0.01% to 2% by weight relative to the total weight of the cosmetic composition.

Preferably, the first cationic surfactant(s) (ii) of the cosmetic composition according to the invention represent from 0.0005% to 12.5% by weight, preferably from 0.001% to 8.5% by weight and more preferentially from 0.003% to 4.5% by weight, better still from 0.1% to 4% by weight, relative to the total weight of the cosmetic composition.

Preferably, the second cationic surfactant(s) (iii) different from the cationic surfactants (ii) of the cosmetic composition according to the invention represent from 0.0005% to 12.5% by weight, preferably from 0.001% to 8.5% by weight and more preferentially from 0.003% to 4.5% by weight relative to the total weight of the cosmetic composition.

This cosmetic composition in particular finds a particularly advantageous application in the hair sector, especially for caring for and/or conditioning the hair.

Advantageously, it is in the form of a conditioning product or alternatively in the form of a hair gel, a lotion or cream or in the form of a mask, in particular for caring for and/or conditioning keratin fibres.

This composition generally has a thickened texture.

This composition is generally opaque.

The examples that follow illustrate the present invention, and should not in any way be considered as limiting the invention.

EXAMPLES

Example 1: Preparation of a First Composition that May be Used in the Process According to the Invention ("Base" Composition)

Composition A was prepared according to table 1 below by mixing the ingredients in the contents indicated as grams of active material.

TABLE 1

| "Base" composition | A |
|---|---|
| Behenyltrimethylammonium methosulfate (Commercial product INCROQUAT BEHENYL TMS from company CRODA comprising 25% by weight of behenyltrimethylammonium methosulfate in cetearyl alcohol) | 1.6 |
| Cetyltrimethylammonium chloride | 1.8 |
| pH agent | qs pH 4.5 ± 0.5 |
| Myristyl alcohol | 7.0 |
| Caprylic/capric acid triglycerides | 7.3 |
| Bis($C_{12}$-$C_{13}$)alkyl 2-hydroxybutanedioate | 0.8 |
| Oxypropyl (10 OP) methylglucoside | 0.9 |
| Propylene glycol | 15 |
| Oxyethylenated polydimethylsiloxane (14 OE) | 1 |
| Fragrance | qs |
| Ethanol | 50 |
| Water | qs 100 g |

Example 2: Preparation of Second Compositions that May be Used in the Process According to the Invention ("Booster" Compositions)

Compositions B1 to C1 were prepared according to table 2 below by mixing the ingredients in the contents indicated as grams of active material.

TABLE 2

| "Booster" compositions | B1 | C1 |
|---|---|---|
| pH agent | qs pH 3.5 ± 0.5 | qs pH 3.5 ± 0.5 |
| Preserving agents | qs | qs |
| Mixture of amino acids of plant origin | — | 0.1 |
| Hexadimethrine chloride | — | 1.35 |
| Amodimethicone (Belsil ADM LOG 1 from Wacker) | — | 2.25 |
| Glycerol | — | 6.8 |
| Cetyltrimethylammonium chloride | 0.75 | 1.5 |
| Pyrodoxine hydrochloride | 0.1 | — |
| D-Biotin | 0.01 | — |
| Water | qs 100 g | qs 100 g |

Example 3: Preparation and Use of the Final Compositions that May be Used in the Process According to the Invention The "base" composition A was mixed with each of the "booster" compositions B1 to C1 in a 1/1 weight ratio to form the final compositions B2 to C2, respectively.

The final compositions are obtained by mixing, using a spatula, of the two compositions and form masks (compositions in cream form) on conclusion of the mixing.

The compositions are applied to the hair at a rate of 12 g of final composition for the entire head of hair, and are then left on the hair for 5 minutes.

The hair is then rinsed and dried.

The final composition B2 leads to good performance qualities in terms of disentangling, smooth feel and coating of the hair.

The final composition C2 leads to good performance qualities in terms of disentangling, a smooth feel and coating of the hair.

Example 4: Instrumental Evaluation of the Compositions 4.1 Composition B2

Composition B2 was evaluated in terms of resistance to breaking during blow drying, compared with a composition B'2 resulting from the mixing of composition A with water, in a 1/1 ratio.

Each of the final compositions is applied to 10 locks of moderately sensitised hair (alkaline solubility 21.6%) measuring 26 cm and weighing 2.7 g previously washed and wrung dry, in a proportion of 1.08 g composition per lock of hair.

After a leave-on time of 5 min, the locks are rinsed. The locks are then blow-dried in a standardized manner: the hairs broken during the operation are meticulously collected and weighed. The lower the amount of broken hairs, the higher the resistance to blow drying.

The means of the relative weights of the hairs broken (expressed in mg/g) during blow drying is given below for each of the compositions.

| | Weight (mg/g) |
|---|---|
| Invention B2 (resulting from the mixing of A + B1) | 18.3 |
| Comparative B'2 (resulting from the mixing of A + water) | 41.8 |

Composition B2 exhibits a 56.2% improvement in the resistance to breaking during blow drying compared with comparative composition B'2.

4.2 Composition C2

Composition C2 was evaluated as regards its influence on the strength of locks of hair, by means of a flexabrasion test.

The flexabrasion test simulates the wear of a hair strand to measure its strength. The device reproduces the real conditions of the stresses inflicted during combing or brushing: extension (when the comb stretches the hair), abrasion (when the fibres rub against each other or on the teeth of the comb) and flexion (when the hairs wind around the comb).

A hair strand, made taut by means of a weight attached to one of its ends, slides while folding on a comb tooth. A device sets it in a to-and-fro motion, of given amplitude and frequency.

The strength of the hair strand is characterized by the time and/or the number of cycles after which the hair strand, subjected to this stress, breaks.

The time before breaking and/or the number of cycles before breaking is proportionately higher the stronger the hair strand.

Clean locks of hair weighing 2.7 g and 26 cm long are treated, on the one hand, with composition C2 derived from the mixing of compositions A and C1, and, on the other hand, with a composition C'2 derived from the mixing of composition A with water, in a 1/1 ratio in both cases, at a rate of 1.08 g of composition per lock of hair. After a leave-on time of 5 minutes, the locks are rinsed and dried.

This treatment (application, rinsing, drying) is repeated five times in total.

After the fifth treatment, 25 hair strands are taken from each lock so as to perform the flexabrasion test on each hair strand.

The median values of the number of cycles and of the time up to breaking are presented below (for 25 hair strands).

|  | Number of cycles | Time (in seconds) |
|---|---|---|
| Treatment with C2 (invention) - 5 applications | 388.5 | 777 |
| Treatment with C'2 (comparative) - 5 applications | 290 | 580 |

It is found that the use of composition C2 leads to a higher number of cycles and to a longer time before breaking than the use of the comparative composition C'2. Composition C2 thus very markedly improves the strength of the hair strands.

The invention claimed is:

1. A cosmetic process for caring and/or conditioning hair comprising:
   (i) a step of mixing at least:
      an anhydrous first composition comprising one or more non-amino oxyethylenated silicones, one or more first cationic surfactants, and less than 10% by weight of water relative to the total weight of the first composition, and
      a second composition comprising water and one or more second cationic surfactants, so as to obtain a final cosmetic composition, and then
   (ii) a step of applying the final cosmetic composition to the hair;
   the one or more non-amino oxyethylenated silicones being non-oxypropylenated; and
   wherein the one or more non-amino oxyethylenated silicones of the first composition are chosen from the compounds of the general formula (II) below:

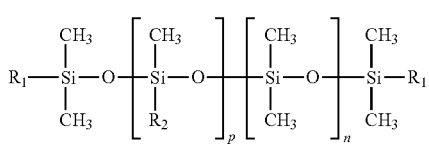

(II)

in which formula (II):
   $R_1$ denotes a methyl radical,
   $R_2$ independently represents a radical —$C_cH_{2c}$—O—$(C_2H_4O)_a(C_3H_6O)_b$—$R_5$,
   a ranges from 2 to 20,
   is 0,
   c is equal to 2 or 3,
   $R_5$ represents a hydrogen atom resulting in a terminal hydroxyl group on R2,
   n ranges from 12 to 100,
   p ranges from 1 to 20;
and wherein the one or more first cationic surfactants of the first composition are chosen from the following compounds:
quaternary ammonium salts of formula (VI) below:

(VI)

in which formula (VI):
   the groups $R_8$ to $R_{11}$ independently represent a linear or branched aliphatic group comprising from 1 to 30 carbon atoms, at least one of the groups $R_8$ to $R_{11}$ denoting a linear or branched aliphatic radical comprising from 12 to 24 carbon atoms, and
   X— is an anion chosen from the group of halides, phosphates, acetates, lactates, ($C_1$-$C_4$)alkyl sulfates, ($C_1$-$C_4$)alkylsulfonates and ($C_1$-$C_4$)alkylarylsulfonates.

2. The process according to claim 1, wherein the first composition comprises less than 9% by weight of water relative to the total weight of the first composition.

3. The process according to claim 1, wherein c is equal to 2.

4. The process according to claim 1, wherein the one or more non-amino oxyethylenated silicones of the first composition represent from 0.01% to 10% by weight relative to the total weight of the first composition.

5. The process according to claim 1, wherein the one or more first cationic surfactants of the first composition and the one or more second cationic surfactants of the second composition are chosen, independently from one another, from cetyltrimethylammonium salts, behenyltrimethylammonium salts, dipalmitoylethylhydroxyethylmethylammonium salts, and mixtures thereof.

6. The process according to claim 1, wherein the one or more first cationic surfactants of the first composition represent a total content of from 0.05% to 15% by weight relative to the total weight of the first composition.

7. The process according to claim 1, wherein the one or more second cationic surfactants of the second composition represent a total content of from 0.05% to 10% by weight relative to the total weight of the second composition.

8. The process according to claim 1, wherein the second composition comprises at least 15% by weight of water relative to the total weight of the second composition.

9. The process according to claim 1, wherein the first and the second compositions are mixed in a first composition/second composition weight ratio ranging from 0.2 to 5.

10. The process according to claim 1, wherein the mixing step is performed just before the application step.

11. The process according to claim 2, wherein the one or more non-amino oxyethylenated silicones of the first composition represent from 0.01% to 10% by weight relative to the total weight of the first composition.

12. The process according to claim 5, wherein the one or more non-amino oxyethylenated silicones of the first composition represent from 0.01% to 10% by weight relative to the total weight of the first composition.

13. The process according to claim 3, wherein the one or more non-amino oxyethylenated silicones of the first composition represent from 0.01% to 10% by weight relative to the total weight of the first composition.

14. A kit comprising at least two compartments:
a first compartment comprising a first anhydrous composition comprising one or more non-amino oxyethylenated silicones, one or more first cationic surfactants, and less than 10% by weight of water relative to the total weight of the first composition,
a second compartment comprising a second composition comprising water and one or more second cationic surfactants;
the one or more non-amino oxyethylenated silicones being non-oxypropylenated and wherein the one or more non-amino oxyethylenated silicones of the first composition are chosen from the compounds of the general formula (II) below:

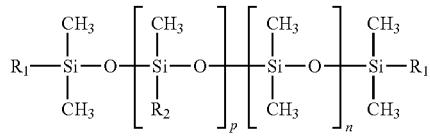

in which formula (II):
$R_1$ denotes a methyl radical,
$R_2$ independently represents a radical —$C_cH_{2c}$—O—$(C_2H_4O)_a(C_3H_6O)_b$—$R_5$,
a ranges from 2 to 20,
b is 0,
c is equal to 2 or 3,
$R_5$ represents a hydrogen atom resulting in a terminal hydroxyl group on $R_2$,
n ranges from 12 to 100,
p ranges from 1 to 20;
and wherein the one or more first cationic surfactants of the first composition are chosen from the following compounds:
quaternary ammonium salts of formula (VI) below:

in which formula (VI):
the groups $R_8$ to $R_{11}$ independently represent a linear or branched aliphatic group comprising from 1 to 30 carbon atoms, at least one of the groups $R_8$ to $R_{11}$ denoting a linear or branched aliphatic radical comprising from 12 to 24 carbon atoms, and
X— is an anion chosen from the group of halides, phosphates, acetates, lactates, ($C_1$-$C_4$)alkyl sulfates, ($C_1$-$C_4$)alkylsulfonates and ($C_1$-$C_4$)alkylarylsulfonates.

* * * * *